US00PP33433P2

(12) United States Plant Patent
Babikow

(10) Patent No.: US PP33,433 P2
(45) Date of Patent: Aug. 31, 2021

(54) ***SCHIZACHYRIUM* PLANT NAMED 'ECGSS'**

(50) Latin Name: *Schizachyrium scoparium*
Varietal Denomination: ECGSS

(71) Applicant: Emerald Coast Growers, LLC, Pensacola, FL (US)

(72) Inventor: Paul David Babikow, Pensacola, FL (US)

(73) Assignee: Emerald Coast Growers, LLC, Pensacola, FL (US)

( * ) Notice: Subject to any disclaimer, the term of this patent is extended or adjusted under 35 U.S.C. 154(b) by 0 days.

(21) Appl. No.: 17/120,174

(22) Filed: Dec. 13, 2020

(51) Int. Cl.
*A01H 5/12* (2018.01)

(52) U.S. Cl.
USPC ..... Plt./384

(58) Field of Classification Search
USPC ..... Plt./384
See application file for complete search history.

*Primary Examiner* — Annette H Para
(74) *Attorney, Agent, or Firm* — Samuel R. McCoy, Jr.

(57) ABSTRACT

A new and distinct cultivar of *Schizachyrium scoparium* plant named 'ECGSS', characterized by the combination of a compact mounded growth habit with arched foliage, green foliage that is longitudinally striped cream yellow in the spring and summer, foliage that becomes progressively suffused with pink towards the apex as the ambient temperature decreases in autumn, strong and resilient foliage that resists lodging in autumn and winter or with exposure to excessive rainfall, and the stability of all characteristics from generation to generation.

3 Drawing Sheets

Latin name of the genus and species: The Latin name of the genus and species of the novel variety disclosed herein is *Schizachyrium scoparium.*

Variety denomination: The novel variety of *Schizachyrium scoparium* disclosed herein has been given the variety denomination 'ECGSS'.

BACKGROUND OF THE INVENTION

Parentage: 'ECGSS' originated as a naturally occurring, whole-plant mutation of *Schizachyrium scoparium* 'The Blues' (not patented). In June of 2015, the inventor discovered the mutation at a commercial greenhouse in Pensacola, Fla. growing amongst a cultivated population of asexually-reproduced *Schizachyrium* 'The Blues' plants. The mutation was noted for its compact habit and uniquely colored foliage and was subsequently isolated for further evaluation in order to confirm the distinctness and stability of the characteristics first observed. Upon confirmation of distinctness and stability, 'ECGSS' was selected for commercialization.

Asexual Reproduction: Asexual reproduction of 'ECGSS' was first accomplished by way of culm division in 2015 at a commercial greenhouse in Pensacola, Fla., and subsequently by way of meristematic tissue culture propagation. Through five subsequent generations, the distinctive characteristics of this cultivar have proven to be stable and true to type.

SUMMARY OF THE INVENTION

The cultivar 'ECGSS' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'ECGSS'. These characteristics in combination distinguish 'ECGSS' as a new and distinct *Schizachyrium* plant cultivar:

1. *Schizachyrium* 'ECGSS' exhibits a compact, densely-foliaged, mounded growth habit with arched foliage and inflorescences held above the foliage; and
2. *Schizachyrium* 'ECGSS' exhibits a short plant height; and
3. *Schizachyrium* 'ECGSS' exhibits strong, upright culms bearing racemes that do not lodge in autumn and winter or with exposure to excessive rainfall; and
4. *Schizachyrium* 'ECGSS' exhibits foliage and inflorescences which persist through winter; and
5. *Schizachyrium* 'ECGSS' exhibits green foliage that is longitudinally striped cream yellow in the spring and summer; and
6. *Schizachyrium* 'ECGSS' exhibits foliage that becomes progressively suffused with pink towards the apex as the ambient temperature decreases in autumn.

BRIEF DESCRIPTION OF THE PHOTOGRAPHS

Colors in the photographs differ slightly from the color values cited in the detailed description, which accurately describes the colors of 'ECGSS'.

DETAILED BOTANICAL DESCRIPTION

Figure 1:
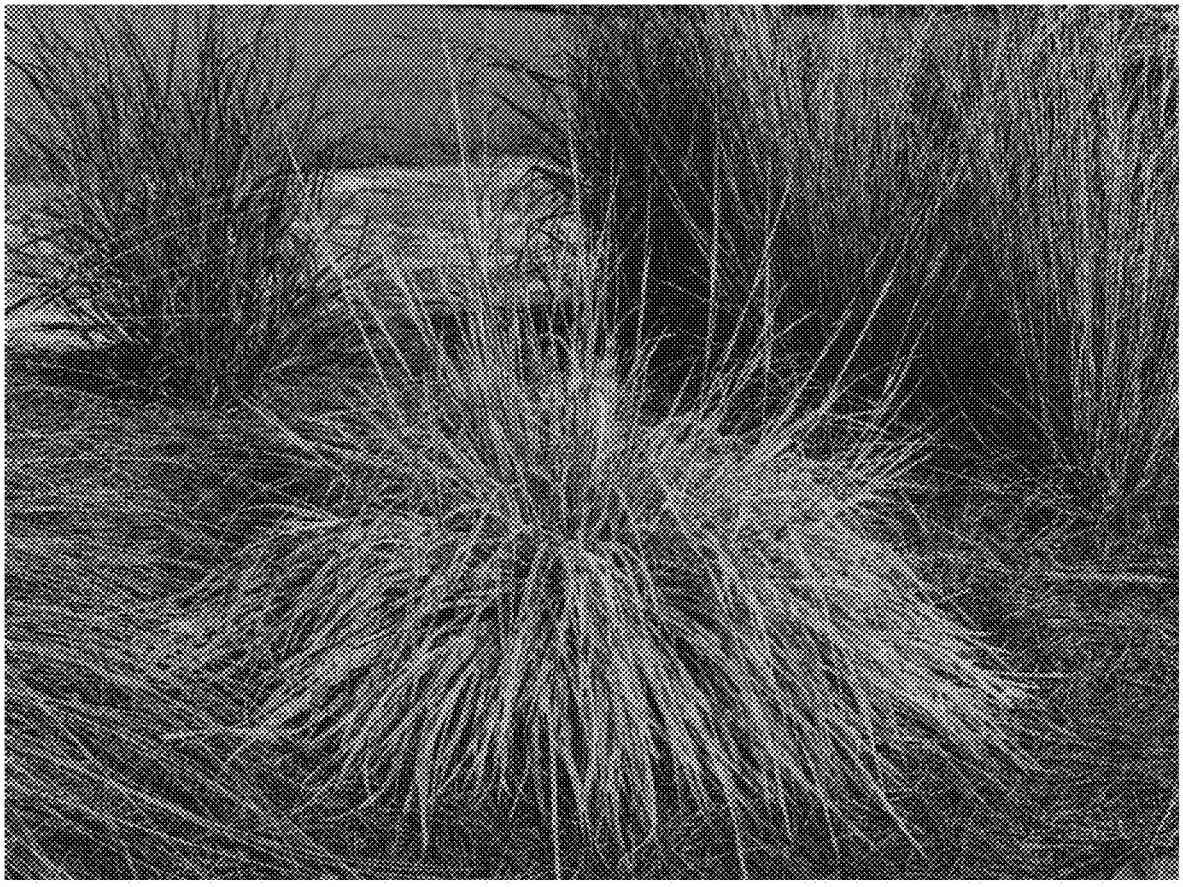
FIG. 1 illustrates, as nearly true as it is reasonably possible to make the same in color illustrations of this type, an exemplary 24 month-old 'ECGSS' plant grown outdoors in the ground, in full sun, in Milton, Fla., as observed in mid-summer.
Figure 2:
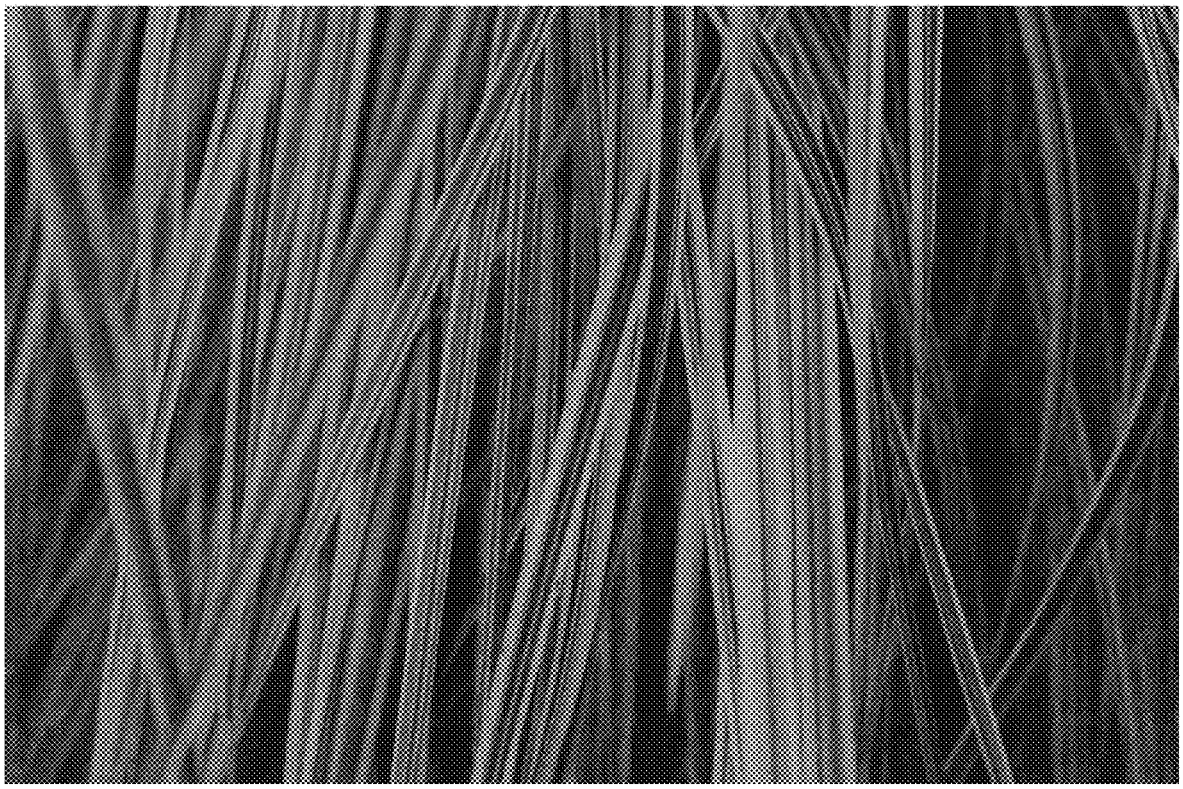
FIG. 2 illustrates, as nearly true as it is reasonably possible to make the same in color illustrations of this type, exemplary mature foliage of a 24 month-old 'ECGSS' plant grown outdoors in the ground, in full sun, in Milton, Fla., as observed in mid-summer.
Figure 3:
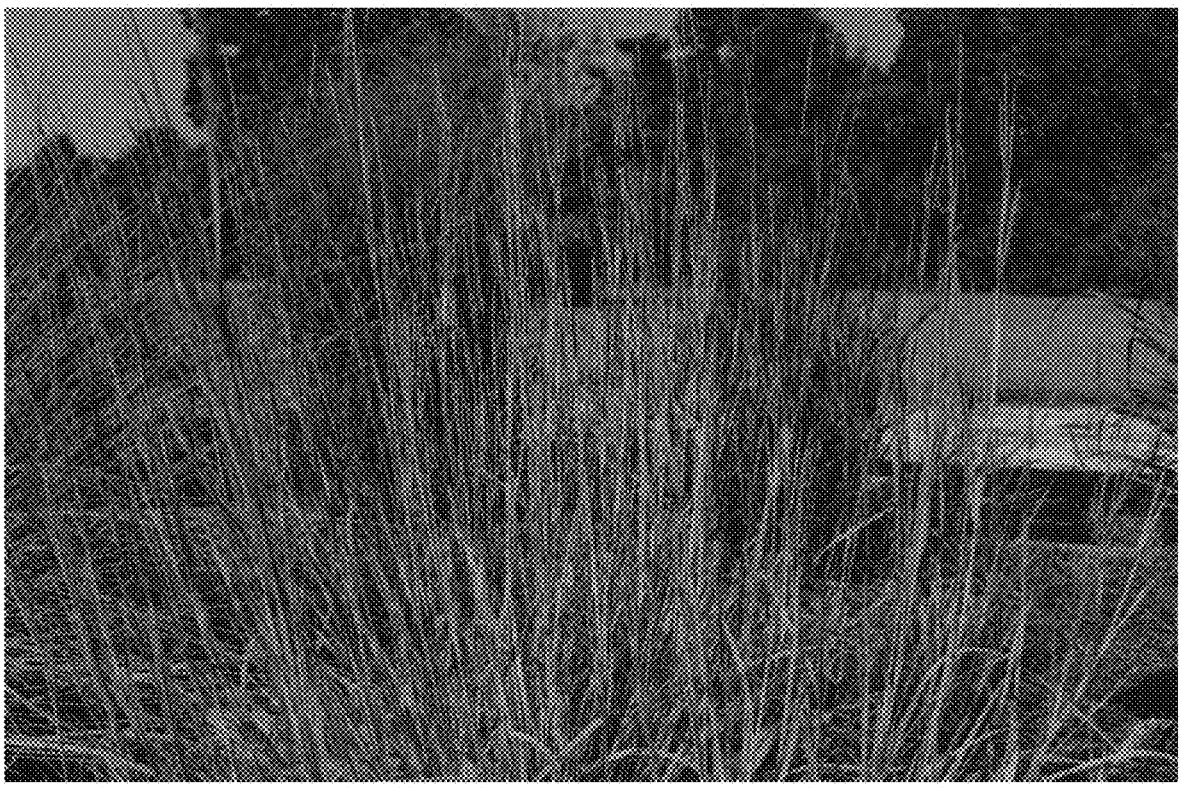
FIG. 3 illustrates, as nearly true as it is reasonably possible to make the same in color illustrations of this type, exemplary inflorescences of a 24 month-old 'ECGSS' plant grown outdoors in the ground, in full sun, in Milton, Fla., as observed in mid-summer.

The following is a detailed botanical description of a new and distinct variety of a *Schizachyrium scoparium* plant known as 'ECGSS'. Unless indicated otherwise, the descriptions disclosed herein are based upon observations in May of 2019, July of 2019, September of 2019, and October of 2019 with the detailed botanical description collected on 24 month-old 'ECGSS' plants grown outdoors in the ground in Milton, Fla. Plants were grown in full sun and maintained using drip irrigation. No fertilizer was applied to the plants and no pest or disease control measures were taken. Plants were not trimmed at any point during observations.

Those skilled in the art will appreciate that certain characteristics will vary with older or, conversely, with younger plants. 'ECGSS' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2007 Fifth edition.

A botanical description of 'ECGSS' and comparisons with the parent and closest known cultivar of *Schizachyrium scoparium* are provided below.

Plant description:

- *Growth habit*.—Herbaceous perennial grass with a compact, mounded growth habit with upright inflorescences held above the foliage.
- *Plant shape*.—Rounded.
- *Average height*.—30 cm from the soil level to the top of the foliar plane; 76 cm from soil level to the top of the floral plane.
- *Plant spread*.—Average of 76 cm.
- *Growth rate*.—Moderately fast.
- *Propagation*.—Method — Culm division and meristematic tissue culture. Time to produce a rooted cutting — Approximately 3 weeks to produce a rooted cutting at approximately 25 degrees Celsius. Time to produce a finished plant — Approximately 12 weeks to produce a marketable finished plant in a one gallon nursery container at approximately 25 degrees Celsius.
- *Disease and pest tolerance or resistance*.—Neither tolerance nor resistance to normal diseases and pests of *Schizachyrium scoparium* has been observed.
- *Environmental tolerances*.—USDA Hardiness Zones 3 through 9.

Root system:

- *General*.—Moderately dense, heavily branched rooting; roots are fibrous and wiry.
- *Distribution in the soil profile*.—Deeply rooted.
- *Color*.—RHS 161C.

Culms:

- *General*.—During the vegetative growth stage, culms are very short and completely obscured by the leaf sheaths. During the reproductive growth stage, the culms elongate and bear a racemose inflorescence. The description below describes elongated culms bearing racemes.
- *Aspect*.—Cylindrical.
- *Culm attitude*.—Erect.
- *Strength*.—Strong.
- *Length*.—30 cm, from base to the apex of the inflorescence.
- *Diameter*.—0.2 cm.
- *Internodal spacing*.—Ranging from 9 to 10 cm.
- *Texture*.—Glabrous, with sheathes villous.
- *Color in summer*.—RHS 184B, and longitudinally striped RHS 158A.
- *Color in autumn*.—RHS 173A.
- *Color in winter*.—RHS 173A.

Foliage:

- *Quantity*.—4 leaves per culm.
- *Attachment*.—Cauline.
- *Division*.—Simple.
- *Length*.—Basal foliage is 32 cm; foliage on the elongated, raceme-bearing culm is 20 cm long.
- *Width*.—0.4 cm.
- *Shape*.—Linear.
- *Apex*.—Acute.
- *Base*.—Sheathed.
- *Sheath*.—Length — 0.3 cm. Aspect — Folded around the culm. Margins — Entire. Texture — Glabrous. Color, summer — RHS 138A, and longitudinally striped with RHS 168A. Color, autumn — RHS 178A and longitudinally striped with RHS 164C.
- *Attitude*.—Upright to arched.
- *Aspect*.—Flat.
- *Margin*.—Entire; not undulate.
- *Texture (adaxial & abaxial surfaces)*.—Glabrous; sparsely pilose at the ligule.
- *Color in summer*.—Juvenile foliage, adaxial surface — RHS 139A, and longitudinally striped with RHS 158B. Juvenile foliage, abaxial surface — RHS N137D, and longitudinally striped with RHS 158A. Mature foliage, adaxial surface — RHS 139A, and longitudinally striped with RHS N155A. Mature foliage, abaxial surface — RHS N137A, and longitudinally striped with RHS NN155B.
- *Color in autumn*.—Juvenile foliage, adaxial surface — RHS 135A, and longitudinally striped with RHS 155A. Juvenile foliage, abaxial surface — RHS 136B, and longitudinally striped with RHS 155C. Mature foliage, adaxial surface — RHS 137A, and longitudinally striped with RHS 155A at the base, becoming longitudinally striped with RHS 181A distally. Mature foliage, abaxial surface — RHS 137A, and longitudinally striped with RHS 158C at the base, becoming longitudinally striped with RHS 182B distally.
- *Color in winter*.—Foliage is dormant in winter; RHS 161C.
- *Venation*.—Pattern — Parallel. Color — All veins are colored the same of surrounding leaf surface.
- *Ligule*.—Membranous; 0.1 cm wide; RHS 161D.

Inflorescence:

- *Inflorescence type and habit*.—Racemose, with alternate pairs of appressed spikelets; spikelets are typically present on the distal 4 cm portion of the inflorescence.

*Natural flowering season*.—August and September in Florida.

*Time to flower*.—5 months.

*Quantity*.—Typically 4 or 5 per node, and typically on the distal three nodes.

*General coloration of the raceme*.—A mixture of RHS 1598 and 1828 in summer; mixture of 161D and 158A in winter.

*Fragrance*.—Non-fragrant.

*Longevity of inflorescence*.—Approximately 2 months.

*Persistence*.—Persistent.

*Rachis*.—Attitude — Upright. Dimensions — 9 cm long and 0.03 cm wide. Color — RHS 15C.

Spikelet buds: To date, flower buds have not been observed.

Spikelets:

*Quantity*.—6 to 10 per raceme.

*Attachment*.—Sessile.

*Arrangement*.—Alternate.

*Spikelet description*.—Only fertile spikelets observed; no sterile spikelets are present. Equal, opposite glumes; 0.7 cm in length and 0.1 cm wide; RHS 130B with longitudinal stripes colored RHS 170D. 2 Lemmas, one lemma extending into very fine, flexuous awn, 0.5 cm in length, RHS 158D in color, and one fine awn approximately 0.8 cm in length; palea small and hyaline.

*Spikelet dimensions*.—Approximately 0.7 cm long, including the awn, and 0.1 cm wide.

*Spikelet hairs*.—Emerging from the base as a tuft surrounding the base; 0.2 mm long and very fine; RHS 155C.

Reproductive organs:

*Androecium*.—Filament — Length — 0.15 cm. Color — RHS 59B. Anthers — Position — Basifixed. Shape — Oblong. Dimensions — 0.25 cm long and 0.05 cm wide. Color — RHS 59B. Pollen — Abundance — Abundant. Color — RHS N182A.

*Gynoecium*.—Pistil — Quantity — One present. Stigmas — Two plumose stigmas on short styles; length is 0.2 cm; width is 0.1 cm; color is RHS 61A. Ovary — Superior; locular; minute, such that size and color are immeasurable.

Caryopsis: Lemma and glumes adhering to the caryopsis; actual caryopsis is very small and fine, less than 0.1 cm wide.

COMPARISON WITH THE PARENT PLANTS AND COMMERCIAL COMPARATOR

Plants of the new cultivar 'ECGSS' differ from the parent, *Schizachyrium scoparium* 'The Blues', in the characteristics described in Table 1 below.

TABLE 1

| Characteristic | 'ECGSS' | 'The Blues' |
|---|---|---|
| Growth habit. | More compact than 'The Blues'. | Less compact and more upright, relative to 'ECGSS'. |
| Strength and resilience of foliage. | Stronger and more resilient; does not lodge in autumn and winter or with exposure to excessive rainfall | Weaker and less resilient; lodges in autumn and winter or with exposure to excessive rainfall |

Plants of the new cultivar 'ECGSS' may be distinguished from the closest known commercial comparator, the common form of the species *Schizachyrium scoparium* 'Blaze' (not patented), by the characteristics described in Table 2.

TABLE 2

| Characteristic | 'ECGSS' | 'Blaze' |
|---|---|---|
| Growth habit. | More compact than 'Blaze'. | Less compact and more upright, relative to 'ECGSS'. |
| Strength and resilience of foliage. | Stronger and more resilient; does not lodge in autumn and winter or with exposure to excessive rainfall | Weaker and less resilient; lodges in autumn and winter or with exposure to excessive rainfall |

That which is claimed is:

1. A new and distinct variety of *Schizachyrium scoparium* plant named 'ECGSS', substantially as described and illustrated herein.

* * * * *